US012766266B2

(12) United States Patent
Somekawa et al.

(10) Patent No.: US 12,766,266 B2
(45) Date of Patent: Oct. 20, 2026

(54) DOSAGE ADJUSTER FOR SYRINGE

(71) Applicant: TAISEI KAKO CO., LTD., Osaka (JP)

(72) Inventors: Tsuyoshi Somekawa, Osaka (JP); Miku Hori, Osaka (JP)

(73) Assignee: TAISEI KAKO CO., LTD., Osaka (JP)

(*) Notice: Subject to any disclaimer, the term of this patent is extended or adjusted under 35 U.S.C. 154(b) by 1096 days.

(21) Appl. No.: 17/785,876

(22) PCT Filed: Dec. 24, 2020

(86) PCT No.: PCT/JP2020/048468

§ 371 (c)(1),
(2) Date: Jun. 15, 2022

(87) PCT Pub. No.: WO2021/132469

PCT Pub. Date: Jul. 1, 2021

(65) Prior Publication Data

US 2023/0017696 A1 Jan. 19, 2023

(30) Foreign Application Priority Data

Dec. 25, 2019 (JP) ................................ 2019-234354

(51) Int. Cl.
*A61M 5/315* (2006.01)

(52) U.S. Cl.
CPC .... *A61M 5/31548* (2013.01); *A61M 5/31553* (2013.01); *A61M 5/31593* (2013.01); *A61M 5/31528* (2013.01)

(58) Field of Classification Search
CPC .......... A61M 5/31536; A61M 5/31553; A61M 5/31593
See application file for complete search history.

(56) References Cited

U.S. PATENT DOCUMENTS 3,815,785 A 6/1974 Gilmont
5,300,041 A * 4/1994 Haber .................... A61M 5/24 604/218
5,531,708 A 7/1996 Woodruff
(Continued)

FOREIGN PATENT DOCUMENTS

JP S60-138545 U 9/1985
JP 2014-526328 10/2014
(Continued)

OTHER PUBLICATIONS

Extended European Search Report for the corresponding European Patent Application No. 20906990.5 issued by the European Patent Office on Dec. 5, 2023.
(Continued)

*Primary Examiner* — Nathan R Price
(74) *Attorney, Agent, or Firm* — Ladas & Parry, LLP

(57) ABSTRACT

Provided is a dosage adjuster for a syringe including: a dosage setting part configured to set the amount of dosage usable out of a liquid medicine filled in the syringe; and a setting restriction part configured to switch between a restricted state in which change in setting of the amount of dosage set by the dosage setting part is restricted and a permissible state in which the change in the setting of the amount of dosage by the dosage setting part is permissible.

4 Claims, 8 Drawing Sheets

(56) References Cited

U.S. PATENT DOCUMENTS

| | | | |
|---|---|---|---|
| 2004/0162528 | A1 | 8/2004 | Horvath et al. |
| 2008/0108952 | A1 | 5/2008 | Horvath et al. |
| 2009/0326479 | A1 | 12/2009 | Janish et al. |
| 2014/0343511 | A1 | 11/2014 | Grunhut |
| 2016/0346455 | A1 | 12/2016 | Cowan |

FOREIGN PATENT DOCUMENTS

| | | | |
|---|---|---|---|
| JP | 2019-88555 | | 6/2019 |
| KR | 101868317 | B1 | 6/2018 |
| WO | 2014164419 | A1 | 10/2014 |

OTHER PUBLICATIONS

First Office Action and search report for the corresponding Taiwanese Patent Application No. 109146339 issued by the Taiwanese Patent Office on Nov. 20, 2023 and its English Translation provided by the foreign associate.
International Search Report for PCT/JP2020/048468(now published as WO2021/132469) mailed on Feb. 16, 2021 and its English translation from WIPO.
Written Opinion for PCT Application PCT/JP2020/048468 issued on Feb. 16, 2021, and its English Translation provided by WIPO.
Internationally Preliminary Report on Patentability for PCT/JP2020/048468 issued on Jun. 28, 2022, and English translation provided by WIPO.

* cited by examiner

DOSAGE ADJUSTER FOR SYRINGE

CROSS-REFERENCE TO RELATED APPLICATIONS

This application is the US national phase filing of PCT Application No. PCT/JP2020/048468, which claims priority to Japanese Patent Application No. 2019-234354, the disclosures of which are incorporated herein by reference in their entireties.

FIELD

The present invention relates to a dosage adjuster for a syringe for adjusting the amount of dosage usable out of a liquid medicine filled in the syringe.

BACKGROUND

Conventionally known is an injector having a structure to adjust the amount of dosage usable out of a liquid medicine filled in a syringe (hereinafter referred to as an adjustment structure) (see, for example, Patent Literature 1). Such an adjustment structure includes a stopper having a cylindrical shape having an inside into which a barrel of the syringe inserted.

The mounting position of the stopper can be changed in a moving direction of a plunger in the state where the plunger is inserted into the barrel. Further, the stopper has a rear end face (i.e., the end face on the rear side in the moving direction) arranged opposite to a front side of a flange of the plunger.

In the aforementioned injector, a space is formed between the stopper and the flange of the plunger by the forward movement of the stopper of the adjustment structure toward the flange of the plunger so that the plunger can be pressed by the amount equivalent to this space.

Therefore, the aforementioned injector is configured to allow a user to use the necessary amount of dosage out of the liquid medicine filled in the syringe when the user moves forward the stopper according to the dosage prescribed by for example, a doctor or a prescription.

Meanwhile, even in the state where the dosage has been set in the adjustment structure, the mounting position of the stopper in the moving direction may be changed when, for example, the flange is strongly pressed. In this case, the user is unable to use the liquid medicine by the amount of dosage as it has been set up.

CITATION LIST

Patent Literature

Patent Literature 1: JP-U S60-138545 A

SUMMARY

Technical Problem

In view of such circumstances, it is an object of the present invention to provide a dosage adjuster for a syringe that enables the user to use the amount of dosage of a liquid solution in the syringe as it has been set.

Solution to Problem

A dosage adjuster for a syringe of the present invention includes: a dosage setting part configured to set the amount of dosage dischargeable out of a liquid medicine filled in the syringe; and a setting restriction part configured to switch between a restricted state in which change in setting of the amount of dosage set by the dosage setting part is restricted and a permissible state in which the change in the setting of the amount of dosage by the dosage setting part is permissible.

In the dosage adjuster for the syringe of the present invention, it can be configured so that the dosage setting part includes a setting operation part configured to rotate in a circumferential direction around a central axis of a plunger of the syringe to thereby change in the setting of the amount of dosage, and the setting restriction part includes a restriction operation part configured to move in a moving direction in which the plunger moves forward and rearward to thereby switch between the restricted state and the permissible state In the dosage adjuster for the syringe of the present invention, it can be configured so that the restriction operation part is configured to switch from the permissible state to the restricted state as the restriction operation part moves in a rearward direction in which the plunger is moved rearward, and configured to switch from the restricted state to the permissible state as the restriction operation part moves in a forward direction in which the plunger is moved forward, and the restriction operation part includes a stopper flange that extends radially outward and orthogonal to the central axis of the plunger.

The dosage adjuster for the syringe of the present invention can be configured to include an operation cylinder that has a cylindrical shape and is configured to, in a state where the syringe is inserted through the operation cylinder, be rotatable in the circumferential direction around the plunger and slidable in the moving direction in which the plunger is moved forward and rearward, wherein the operation cylinder includes the dosage setting part and the setting restriction part.

In the dosage adjuster for the syringe of the present invention, it can be configured so that the dosage setting part includes a movable receiving part that is arranged on an opposite side of a front surface of a flange of the plunger of the syringe and is movable forward in the moving direction of the plunger from a position in contact with the front surface of the flange, and the movable receiving part is configured to set the amount of dosage on the basis of a distance away from the flange in the forward direction.

DESCRIPTION OF EMBODIMENTS

Hereinafter, a dosage adjuster for a syringe (hereinafter referred to as the dosage adjuster) according to an embodiment of the present invention will be described with reference to the attached drawings.

The dosage adjuster is an instrument used for, for example, fixing the amount of dosage (that is, an amount to be administered) in a liquid medicine filled in a syringe which is usable (dischargeable) according to the dosage prescribed by, for example, a doctor or a prescription. The amount of dosage usable out of the liquid medicine herein means an amount of dosage of the liquid medicine which can be discharged by a single pressing operation of a plunger.

Figure 7A:
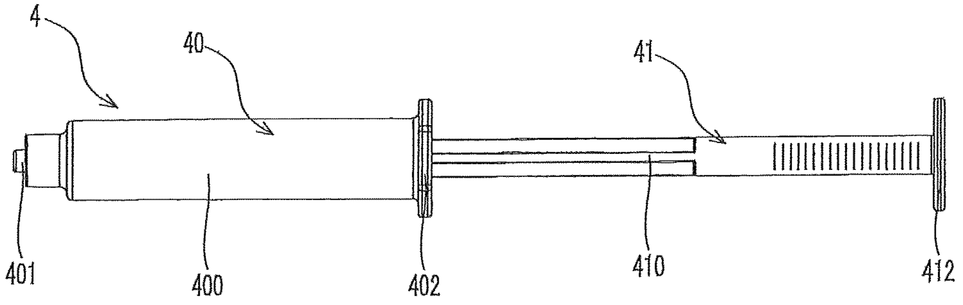
FIG. 7A is a side view of a syringe to which the dosage adjuster for the syringe according to the embodiment is attached.

The description will be given on the syringe prior to the description on the dosage adjuster. As shown in FIG. 7A, the syringe 4 includes a barrel 40 to be filled with a solution such as liquid medicine and a plunger 41 to eject the liquid medicine filled in the barrel 40.

The barrel 40 includes a cylindrical part 400, a nozzle 401 provided at one end in an axial direction of the cylindrical part 400, and an annular flange 402 extending outward (i.e., radially outward of the cylindrical part 400) from the entire outer circumference at the other end in the axial direction of the cylindrical part 400.

Figure 7B:
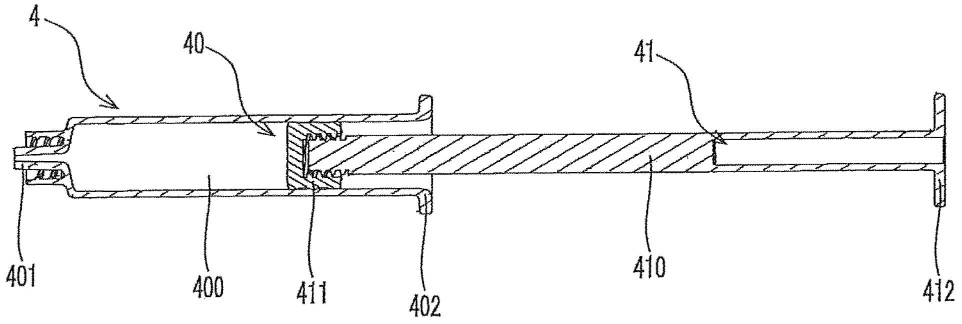
FIG. 7B is a vertical cross section view of the syringe to which the dosage adjuster for the syringe according to the embodiment is attached.

As shown in FIG. 7B, the plunger 41 includes a shaft-like rod part 410, a gasket 411 attached to a distal end (i.e., one end in a longitudinal direction) of the rod part 410 and being in close contact with the entire circumference of an inner peripheral surface of the cylindrical part 400, and an operation part 412 formed on a rear end (i.e., the other end in the longitudinal direction) of the rod part 410.

The operation part 412 is formed into a flange shape extending from the rod part 410 and has a plate surface on one side arranged to face forward in the moving direction of the plunger 41 and a plate surface on the other side arranged to face rearward in the moving direction of the plunger 41. More specifically, the one surface of the operation part 412 is arranged to face forward in the moving direction of the plunger 41, and the other surface of the operation part 412 is arranged to face rearward in the moving direction of the plunger 41. Further, an outer shape of the operation part 412 is larger than that of the rod part 410, and the entire circumference of an outer peripheral edge of the operation part 412 is located outside the rod part 410.

The operation part 412 is a part that the user presses to move the plunger 41 forward and that comes into contact with a movable receiving part 21 of a dosage setting part 2 to be described later. However, it can be configured such that the operation part 412 serves as a flange that is pressed for moving the plunger 41 forward, and a flange other than the operation part 412 is formed on the front side of the operation part 412 to allow the other flange to come into contact with the movable receiving part 21 of the dosage setting part 2 to be described later. (see FIG. 8D and FIG. 8E).

In this embodiment, the following description will be made by referring to a direction in which the plunger 41 moves as a moving direction, a direction in which the plunger 41 moves forward (i.e., the direction in which the plunger 41 is pressed into the barrel 40) in the moving direction as the forward direction, and a direction in which the plunger 41 moves backward in the moving direction (i.e., the direction in which the plunger 41 is pulled out from the barrel 40) as a backward direction.

Figure 1:
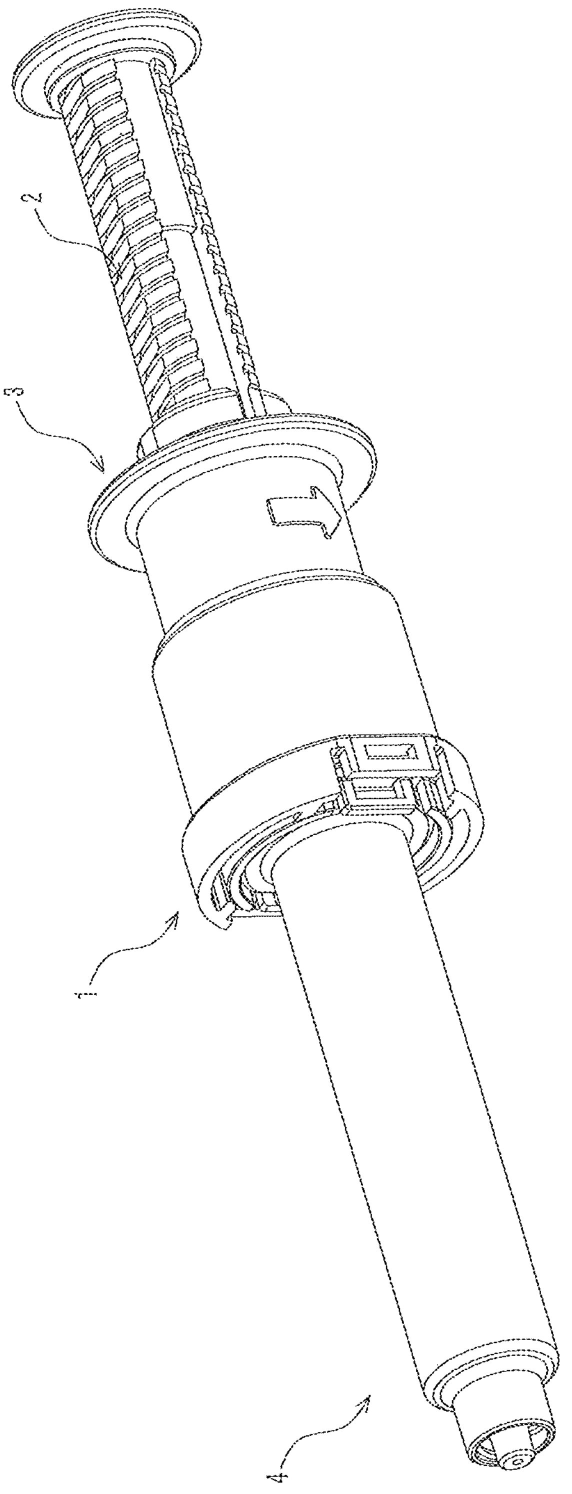
FIG. 1 is a perspective view of a dosage adjuster for a syringe according to an embodiment of the present invention in a preparation kit of the dosage adjuster.

As shown in FIG. 1, the dosage adjuster 1 includes a dosage setting part 2 configured to set the amount of dosage to be usable out of the liquid medicine filled in the syringe 4, and a setting restriction part 3 that can switch between a restricted state in which change in the setting in the amount of dosage by the dosage setting part 2 is restricted and a permissible state in which change in the setting in the amount of dosage by the dosage setting part 2 is allowed.

In the following description of this embodiment, the setting of the amount of dosage out of the liquid medicine filled in the syringe 4 will be referred to as the setting in the amount of dosage.

Figure 2:
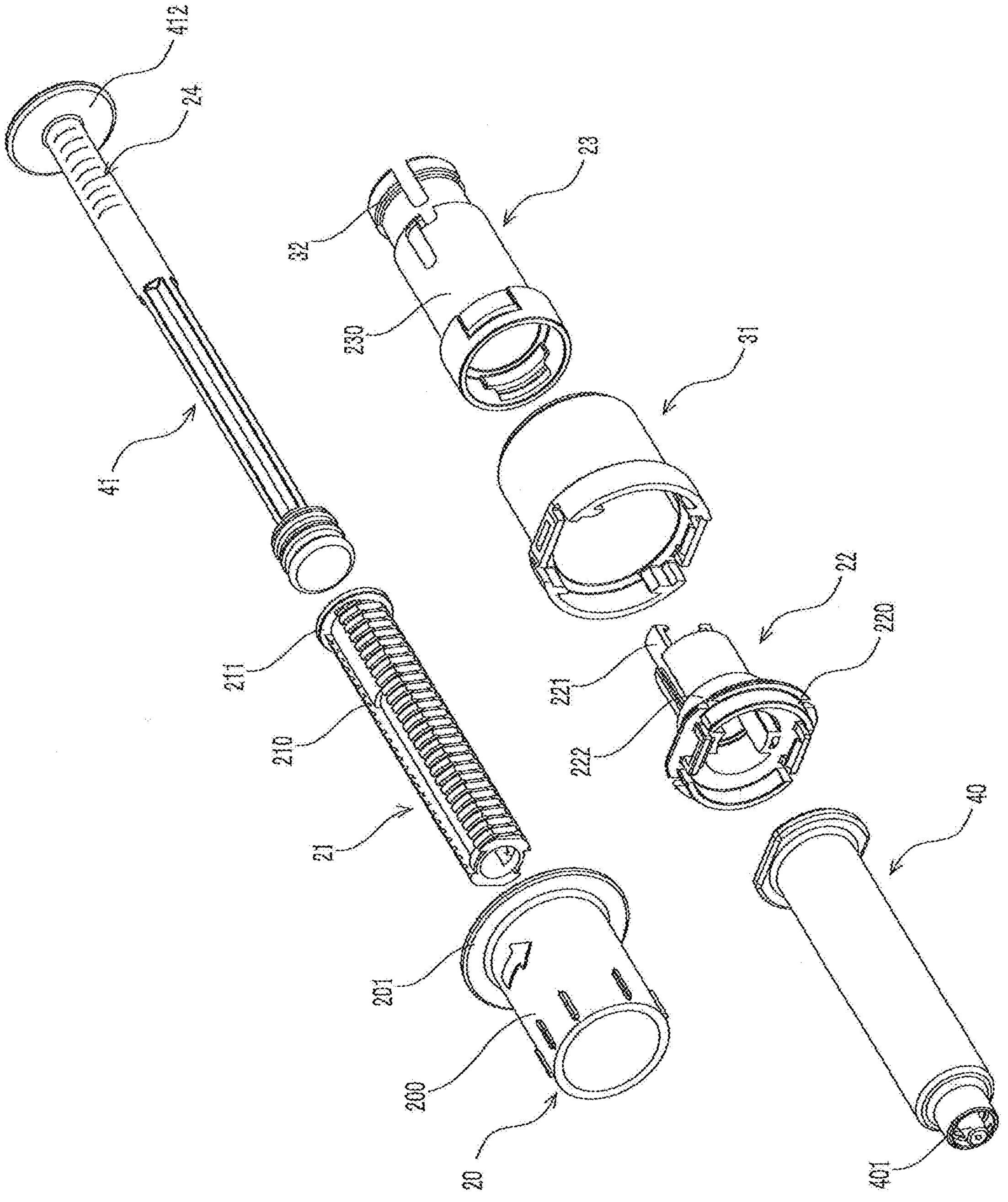
FIG. 2 is an exploded perspective view of the dosage adjuster for the syringe according to the embodiment.

As shown in FIG. 2, the dosage setting part 2 includes a setting operation part 20 that is configured to be rotated in a circumferential direction around the plunger 41 to change the setting in the amount of dosage, the movable receiving part 21 that is arranged on the front side of the operation part to be opposed to each other and movable in the moving direction, a connecting part 22 that connects the movable receiving part 21 and the barrel 40, an interlock mechanism 23 that moves the movable receiving part 21 in the moving direction in association with the rotational motion of the setting operation part 20, and a scale 24 that allows to measure the moving distance toward the front side in the moving direction of the movable receiving part 21.

Figure 3:
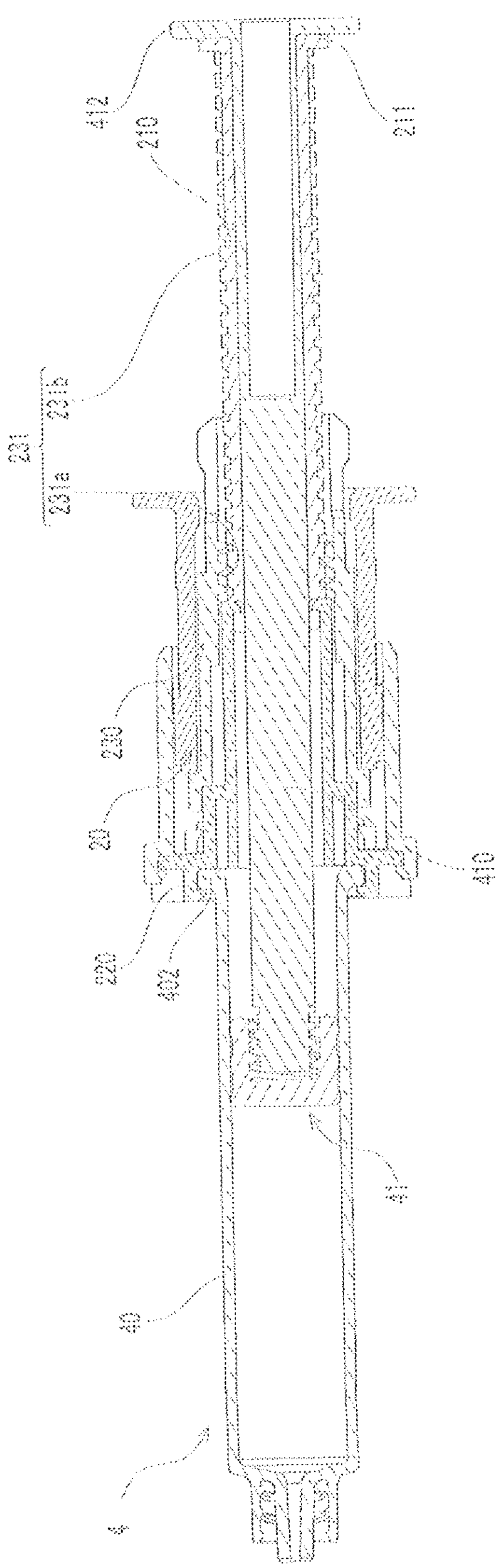
FIG. 3 is a cross section view of the dosage adjuster for the syringe according to the embodiment and the syringe.

The setting operation part 20 has a cylindrical shape and arranged with its axial direction along with the moving direction. As shown in FIG. 3, the rod part 410 is inserted and housed in the setting operation part 20. Further, the setting operation part 20 is configured to be able to rotate relative to the syringe 4. Thus, the setting operation part 20 is configured to rotate (rotate around its axis) in a circumferential direction around the rod part 410 while surrounding the rod part 410.

As shown in FIG. 2, the setting operation part 20 of this embodiment includes a cylindrical operation cylinder 200 having a cylinder shape, and a stopper flange 201 extending radially outward from the outer peripheral surface of the operation cylinder 200.

One end in the axial direction of the operation cylinder 200 is a front end located on the nozzle 401 side, and the other end in the axial direction of the operation cylinder 200 is a rear end located on the operation part 412 side of the plunger 41.

The stopper flange 201 that is continuous along the entire circumference of the operation cylinder 200 in the circumferential direction has thus an annular shape and is formed on the rear end side of the operation cylinder 200.

The movable receiving part 21 includes a rod insertion part 210 having a cylindrical shape and allowing the rod part 410 to be inserted in the rod insertion part 210, and a receiving part 211 provided in the rod insertion part 210 to receive the operation part 412 of the plunger 41 on the rear end side in the moving direction.

The rod insertion part 210 is relatively rotatable to the rod part 410 in the moving direction, while the inner peripheral surface of the rod insertion part 210 and the outer peripheral surface of the rod part 410 are in contact with each other. The axial direction of the rod insertion part 210 is the same as the moving direction.

As shown in FIG. 3, the receiving part 211 is formed at a rear end of the rod insertion part 210 (i.e., the rear end in the moving direction). A rear end surface in the moving direction of the receiving part 211 faces a front surface of the operation part 412. Accordingly, when the rod insertion part 210 is moved forward relative to the operation part 412, a space is formed between the rear end surface of the receiving part 211 and the front surface of the operation part 412. When the operation part 412 (plunger 41) is moved forward relative to the rod insertion part 210, the rear end surface of the receiving part 211 comes into contact with the front surface of the operation part 412.

In this manner, the amount of dosage obtained by the pressing operation against the plunger 41 by a single pressing operation (hereinafter referred to as the allowance amount for the pressing operation) is fixed by the distance by which the receiving part 211 is moved away from the operation part 412 in the forward direction, that is, by the position of the receiving part 211 relative to the moving direction.

Figure 4A:
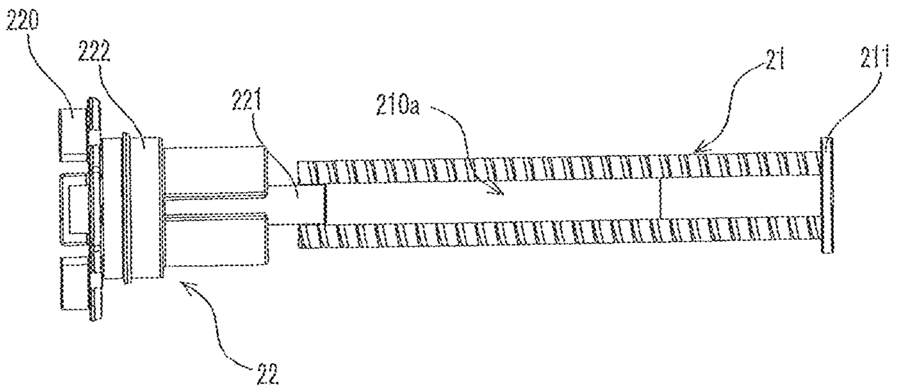
FIG. 4A is an external view of a structure to guide a movement of a movable receiving part of the dosage adjuster for the syringe according to the embodiment.

As shown in FIG. 4A, the connecting part 22 includes a fixing part 220 that is fixed to the barrel 40 in the state where the rotation is restricted, a guide part 221 that is provided in the fixing part 220 and configured to guide the movable receiving part 21 in the moving direction, and an attachment part 222 that attaches the interlock mechanism 23 (more specifically, an interlock rotating part 230 to be described later) in a rotatable state.

The fixing part 220 according to this embodiment is configured to embrace a rear end of the barrel 40 (more specifically, the flange 402 of the barrel 40) (see FIG. 3).

The guide part 221 extends rearward from the fixing part 220 in the moving direction and is formed to enter a long hole 210*a* that is formed in the rod insertion part 210.

Here, the long hole 210*a* is formed to extend along the axial direction (i.e., the longitudinal direction) of the rod insertion part 210. Two long holes 210 are formed in the rod insertion part 210 of this embodiment, but the number of long hole(s) 210*a* can be one or three or more.

Figure 4B:
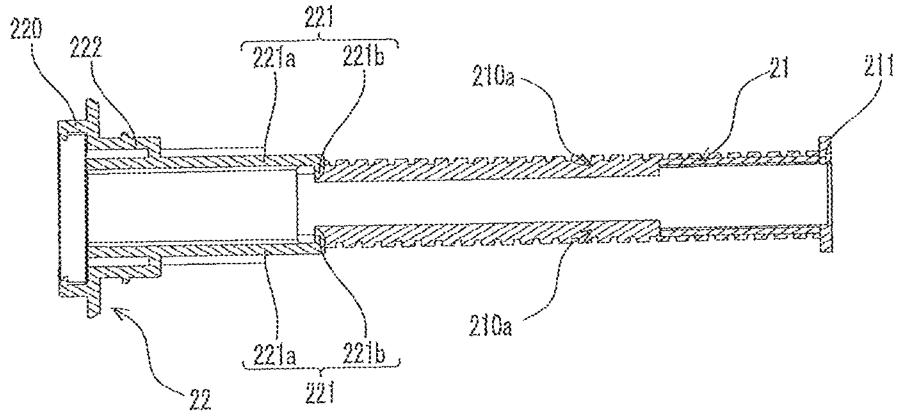
FIG. 4B is a vertical cross section view of the structure to guide the movement of the movable receiving part of the dosage adjuster for the syringe according to the embodiment.

As shown in FIG. 4B, the guide part 221 of this embodiment includes an extending part 221*a* that extends rearward from the attachment part 222 in the moving direction, and a protruding part 221*b* that protrudes inward from the extending part 221*a* and is configured to enter the long hole 210*a* of the rod insertion part 210.

The protruding part 221*b* is configured to contact an edge (i.e., the longitudinal side edge) that constitutes the long hole 210*a* in the circumferential direction. Thus, the protruding part 221*b* is configured to allow the rod insertion part 210 to move in the moving direction, while preventing the rod insertion part 210 from rotating in the circumferential direction. As described above, the connecting part 22 is a structure to allow the movable receiving part 21 to move along the moving direction while preventing the movable receiving part 21 from rotating.

In the connecting part 22, the guide parts 221 of the same number as that of the long holes 210*a* of the rod insertion part 210 are formed. Accordingly, the guide parts 221 which are separately provided are respectively inserted into the long holes 210*a* of the rod insertion part 210.

The attachment part 222 is formed into a cylindrical shape, on which the interlock rotating part 230 in the state where it is rotatable and prevented from being pulled out is fitted.

Figure 6A:
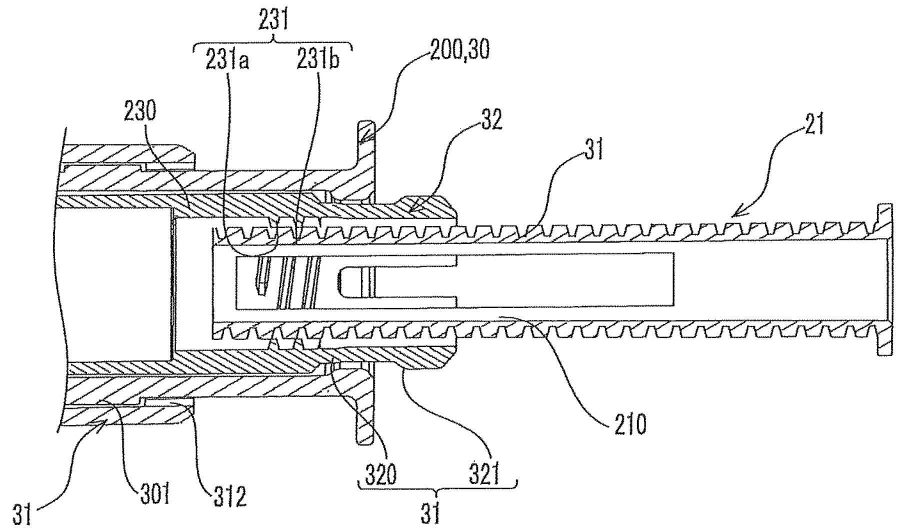
FIG. 6A is an explanatory view of the mechanism to restrict movement of the movable receiving part of the dosage adjuster for the syringe according to the embodiment in the state before the movement of the movable receiving part is restricted.

As shown in FIG. 6A, the interlock mechanism 23 includes the interlock rotating part 230 that is configured to rotate in the circumferential direction in association with the rotation of the setting operation part 20 (i.e., rotates in association with the setting operation part 20) while being arranged in the setting operation part 20, and a power transmission part 231 that is provided in the interlock rotating part 230 and the rod insertion part 210 and that allows the rod insertion part 210, which receives the rotating interlock rotating part 230 in the circumferential direction, to move in the moving direction.

In the interlock rotating part 230, a fitting groove 230*a* (see FIG. 5A) that allows a protrusion 204 (see FIG. 5B) protruding radially inward from the inner peripheral surface of the setting operation part 20 to fit into the fitting groove 203*a*.

Figure 5A:
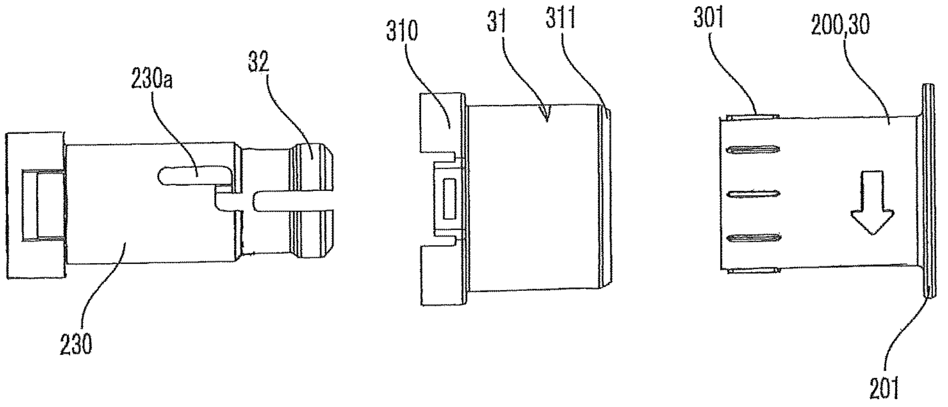
FIG. 5A is an external view of a mechanism of the dosage adjuster for the syringe according to the embodiment to change the setting in the amount of dosage, restrict the change of the setting in the amount of dosage, and release the restriction.

As shown in FIG. 5A, the fitting groove 230*a* is formed to extend along the moving direction. The protrusion 204 fitted into the fitting groove 230*a* is restricted from moving in the same direction as the rotation direction of the setting operation part 20 by side surfaces constituting the fitting groove 230*a*, while being allowed to move in the moving direction. Thus, the setting operation part 20 is configured to be restricted from rotating around the interlock rotating part 230 to thereby rotate in association with the interlock rotating part 230, while being allowed to slide relative to the interlock rotating part 230 in the moving direction.

As shown in FIG. 3, the power transmission part 231 includes an inward screw part 231*a* that is formed on the inner peripheral surface of the interlock rotating part 230, and an outward screw part 231*b* that is formed on an outer surface of the rod insertion part 210 and configured to come into threaded engagement with the inward screw part 231*a*.

The inward screw part 231*a* is formed by a female screw and the outward screw part 231*b* is formed by a male screw. The rotation in the circumferential direction of the rod insertion part 210 is restricted by the guide part 221 so that the rod insertion part 210 moves in the moving direction without rotation when the interlock rotating part 230 is rotated.

As shown in FIG. 2, the scale 24 is formed in the rod part 410 of the plunger 41. Further, marks of the scale 24 are formed to indicate larger value (value representing the amount of dosage of a liquid medicine which can be used) toward the front side with reference to the position of the operation part 412. The setting of the amount of dosage is made by aligning the position of the rear end surface of the receiving part 211 of the movable receiving part 21 with the position of the mark on the scale 24 indicating the value representing the amount of dosage to be used. That is, the scale 24 is provided to measure the amount of dosage as an amount usable.

Figure 5B:
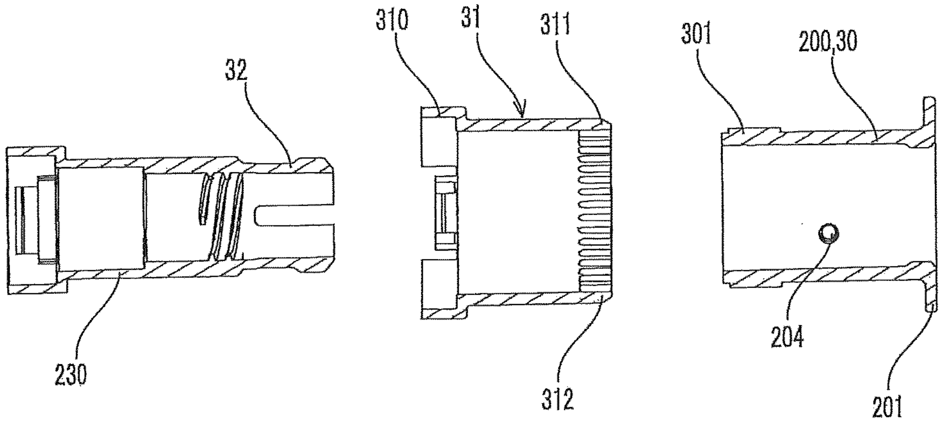
FIG. 5B is a vertical cross section view of the mechanism of the dosage adjuster for the syringe according to the embodiment to change the setting in the amount of dosage, restrict the change of the setting in the amount of dosage, and release the restriction.

As shown in FIG. 5B, the setting restriction part 3 includes a restriction operation part 30 that is slidable relative to the syringe 4 in the moving direction, an anti-rotation part 31 that restricts the rotational movement of the setting operation part 20 as the restriction operation part 30 slides in the backward direction, and a movement restriction part 32 that restricts the movable receiving part 21 from moving in the moving direction as the restriction operation part 30 slides in the backward direction.

The restriction operation part 30 of this embodiment is formed by the operation cylinder 200. That is, the restriction operation part 30 is a part to be operated when the set amount of dosage of the liquid medicine is changed, the change in the set amount of dosage is restricted, and the restriction is released.

The anti-rotation part 31 has a cylindrical shape and includes a front end part 310 that is fixed to the connecting part 22 in the state where the rotation (rotation around its axis) in the circumferential direction around the plunger 41 is restricted, and a rear end part 311 that allows the operation cylinder 200 to insert into the rear end part 311 while being in a slidable state.

The anti-rotation part 31 is configured to allow the operation cylinder 200 to rotate in the circumferential direction in the state where the operation cylinder 200 moves forward toward the front end part 310 side, and configured to restrict the rotation of the operation cylinder 200 in the circumferential direction in the state where the operation cylinder 200 is moved rearward toward the rear end part 311 side.

As shown in FIG. 5B, the anti-rotation part 31 according to this embodiment includes anti-rotation projections 312 formed to project radially inward from the inner peripheral surface of the rear end part 311 and extend straight along the axial direction.

Figure 6B:
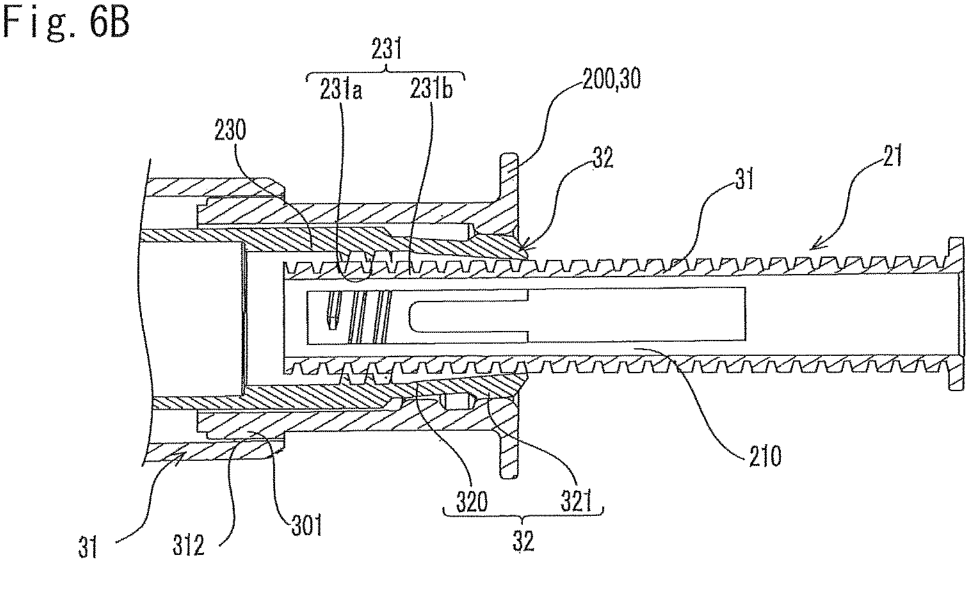
FIG. 6B is an explanatory view of the mechanism to restrict movement of the movable receiving part of the dosage adjuster for the syringe according to the embodiment in the state where the movable receiving part is restricted from sliding.

As shown in FIG. 6A, the anti-rotation projections 312 are out of engagement in the circumferential direction from interfering projections 301 that project radially outward from the outer peripheral surface of the front end part of the operation cylinder 200 in the state where the operation cylinder 200 is moved forward. On the other hand, as shown in FIG. 6B, the anti-rotation projections 312 interfere (come into contact with) the interfering projections 301 in the circumferential direction in the state where the operation cylinder 200 is moved rearward.

The interfering projections 301 and the operation cylinder 200 form the restriction operation part 30. Each of the interfering projections 301 has a shape extending along the same direction as the longitudinal direction of the anti-rotation projection 312 (see FIG. 5A).

A plurality of anti-rotation projections 312 aligning at certain intervals along the entire circumference in the circumferential direction are formed on the inner peripheral surface of the rear end part 311 (see FIG. 5B). The distance between each two adjacent anti-rotation projections 312 in the circumferential direction is substantially the same as the width of each of the interfering projections 301. When the operation cylinder 200 slides forward, each of the interfering projections 301 enters between each two adjacent anti-rotation projections 312.

As the insertion portions for the interfering projections 301 are thus provided along the entire circumference of the inner peripheral surface of the rear end part 311, it is easy to bring each adjacent ones of the anti-rotation projections 312 and the interfering projections 301 into the state where they are interfered with each other without rotating the operation cylinder 200 after the amount of dosage of the liquid medicine has been set. Therefore, the dosage adjuster 1 of this embodiment enables to switch the operation cylinder 200 from the aforementioned allowed state to the restricted state, while maintaining the amount of dosage of the liquid medicine set at the operation cylinder 200.

A plurality of interfering projections 301 are formed in the operation cylinder 200 of this embodiment, but a single interfering projection 301 can be formed in the operation cylinder 200.

As shown in FIG. 6A and FIG. 6B, the movement restriction parts 32 are arranged in the outer peripheral surface of the movable receiving part 21 on the sides opposite to each other. Thus, the interlock rotating part 230 and the movement restriction part 32 are arranged inside the operation cylinder 200, the movable receiving part 21 is arranged inside the interlock rotating part 230 and the movement restriction part 32, and the rod part 410 of the plunger 41 is inserted into the movable receiving part 21.

The movement restriction part 32 is pressed in the direction toward the movable receiving part 21 by the rearward movement of the operation cylinder 200, and the movement restriction part 32 is released from the pressure by the operation cylinder 200 by the forward movement of the operation cylinder 200. Further, the movement restriction part 32 is configured to come into contact with the outer surface of the movable receiving part 21 when it is pressed to the operation cylinder 200, and configured to separate from the outer surface of the movable receiving part 21 when it is released from the pressure by the operation cylinder 200.

The movement restriction part 32 according to this embodiment includes a flexible piece part 320 that is formed to extend rearward in the moving direction from the rear end of the interlock rotating part 230 and has flexibility, and a bulging part 321 that bulges outward from the outer surface of the flexible piece part 320.

Thus, it is configured so that, when the operation cylinder 200 is moved rearward, the bulging part 321 is pressed radially inward by the inner peripheral edge on the rear end side of the operation cylinder 200, to thereby allow the flexible piece part 320 to come into contact with the outer peripheral surface of the movable receiving part 21.

The structure of the dosage adjuster 1 according to this embodiment is described as above. Subsequently, the usage of the dosage adjuster 1 will be described with reference to the attached drawings.

Figure 8A:
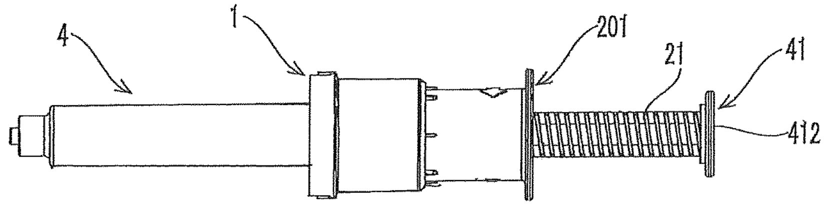
FIG. 8A is an explanatory view of usage of the dosage adjuster for the syringe according to the embodiment, specifically a view when it is not used.
Figure 8B:
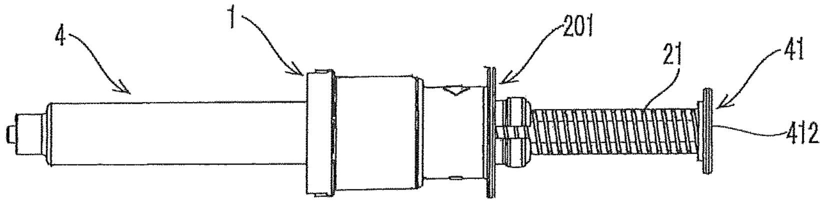
FIG. 8B is an explanatory view of the usage of the dosage adjuster for the syringe according to the embodiment, specifically a view in the state where it allows a change in setting of the amount of dosage.

In the dosage adjuster 1 when it is not used, the setting restriction part 3 is switched to the restricted state as shown in FIG. 8A, and thus the operation cylinder 200 is slid forward to switch the setting restriction part 3 to the permissible state as shown in FIG. 8B.

Figure 8C:
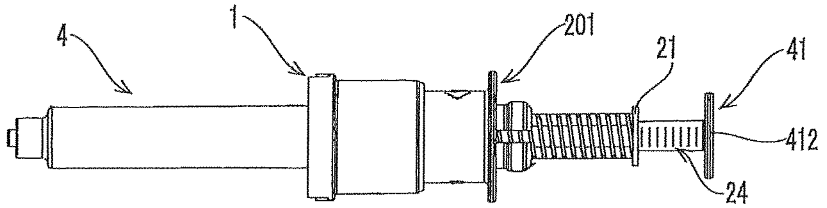
FIG. 8C is an explanatory view of the usage of the dosage adjuster for the syringe according to the embodiment, specifically a view in which the setting of the amount of dosage is being changed.
Figure 8D:
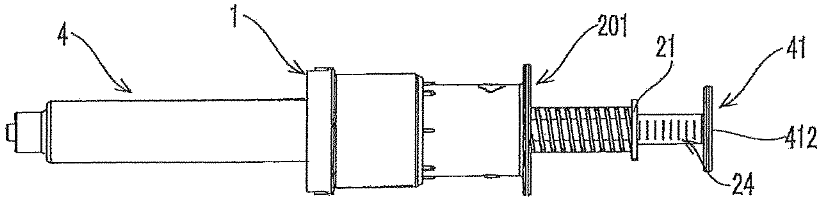
FIG. 8D is an explanatory view of the usage of the dosage adjuster for the syringe according to the embodiment, specifically a view in which the change in the setting of the amount of dosage is restricted.

Subsequently, the operation cylinder 200 is rotated to allow the movable receiving part 21 to move forward to the operation part 412 as shown in FIG. 8C to thereby fix an allowance amount for pressing the plunger 41, that is, fix the setting of the amount of dosage of the liquid medicine. Thereafter, as shown in FIG. 8D, the operation cylinder 200 is slid in the rearward direction to switch the setting restriction part 3 from the permissible state to the restricted state.

Figure 8E:
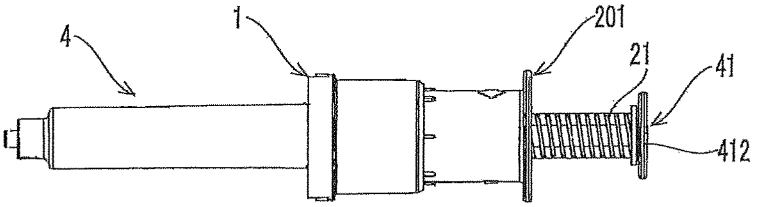
FIG. 8E is an explanatory view of the usage of the dosage adjuster for the syringe according to the embodiment, specifically a view in which the liquid medicine of the set amount of dosage has been discharged, while the change in the setting of the amount of dosage is restricted.

Then, as shown in FIG. 8E, the plunger 41 is moved forward until the operation part 412 comes into contact with the movable receiving part 21 so that the set amount of dosage of the liquid medicine can be discharged from the syringe 4. In order to move the plunger 41 forward, the user only has to press the plunger 41 with the thumb placing on the operation part 412 and the other fingers hooked on the stopper flange 201.

Figure 8F:
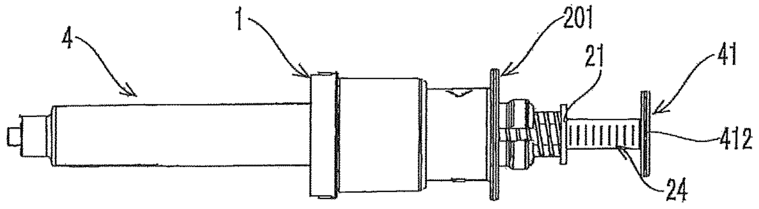
FIG. 8F is an explanatory view of the usage of the dosage adjuster for the syringe according to the embodiment, specifically a view in the state where the setting in the amount of dosage is changed again.

When the operation cylinder 200 is slid forward to switch the setting restriction part 3 from the restricted state to the permissible state as shown in FIG. 8F, it is possible to set the amount of dosage of the liquid medicine again.

After the syringe 4 is used once, it is confirmed that the setting restriction part 3 is in the restricted state and then stored in, for example, a safety cabinet.

In the case where the liquid medicine in the syringe 4 is desired to be used again, the operation cylinder 200 is slid forward to switch the setting restriction part 3 from the restricted state to the permissible state, followed by rotating the operation cylinder 200 to perform the setting of the amount of dosage of the liquid medicine, then sliding the operation cylinder 200 in the rearward direction to switch the setting restriction part 3 from the permissible state to the restricted state, and moving the plunger 41 forward until the operation part 412 comes into contact with the movable receiving part 21. Thereby, the liquid medicine by the amount of dosage newly set can be discharged from the syringe 4.

According to the dosage adjuster 1 according to this embodiment, the restricted state and the permissible state can be switched by the setting restriction part 3 as described above. Thus, it is possible to prevent the setting of the amount of dosage from changing at an unintentional timing of the user by: switching into the permissible state by the setting restriction part 3 when the amount of dosage usable out of the liquid medicine filled in the syringe 4 is set; and switching into the restricted state by the setting restriction part 3 after the setting of the amount of dosage is completed.

Accordingly, the dosage adjuster 1 can produce an excellent effect of enabling the user to use the liquid medicine within the syringe by the amount of dosage according to the set amount.

Further, the operation directions among the direction to operate the setting operation part 20 that is provided to change the setting in the amount of dosage of the liquid medicine to be usable, and the direction to operate the restriction operation part 30 that is provided to restrict the change in setting of the amount of dosage by the dosage setting part 2 and release the restriction, that is, provided to switch between the restricted state and the permissible state are different from each other. Thus, it is possible to suppress unintentional change in the setting of the amount of dosage, or unintentional switching between the restricted state and the permissible state caused by erroneous operation.

Moreover, since the user can press the plunger 41 with the thumb placing on the operation part 412 of the plunger 41 and the other fingers hooking on the front surface of the stopper flange 201, a force directed in a rearward direction (i.e., in a direction in which the plunger 41 is moved rearward) in the moving direction (i.e., a force in a direction in which the operation part 412 of the plunger 41 and the stopper flange 201 come close to each other) is applied to the stopper flange 201 when the liquid medicine in the syringe 4 is ejected by the plunger 41.

According to the dosage adjuster 1, since a single member enables the setting of the amount of dosage of the liquid medicine and enables the switching between the restricted state and the accepted state, it is also possible to improve the operability.

Here, the restriction operation part 30 is configured to switch from the permissible state to the restricted state as the restriction operation part 30 is operated to slide in the rearward direction. Thus, in the case where the restriction operation part 30 is not switched to the restricted state when the plunger 41 is pressed, a force in a direction in which the operation part 412 of the plunger 41 and the stopper flange 201 come close to each other. Accordingly, it is possible to allow the restriction operation part 30 to slide to thereby switch from the permissible state to the restricted state or it is possible to make the user aware that the operational state is not switched from the permissible state to the restricted state.

In the dosage adjuster 1, even in the case where the liquid medicine filled in the syringe 4 is divided and used multiple times, the amount of dosage can be set by moving forward the receiving part 211 of the dosage setting part 2 with reference to the state where the operation part 412 contacts the receiving part 211 of the dosage setting part 2. Therefore, the dosage adjuster 1 for the syringe having the above structure is configured to set the amount or distance by which the receiving part 211 of the dosage setting part 2 is moved forward, constantly with reference to the position of the operation part 412. Thereby, it is possible to simply and accurately set the amount of dosage usable out of the liquid medicine.

The dosage adjuster for the syringe of the present invention is not limited to the aforementioned embodiment, and it is matter of course that various modifications can be made without departing from the gist of the present invention.

Although not specifically mentioned in the aforementioned embodiment, the syringe 4 can be a syringe filled with the liquid medicine (so-called a pre-filled syringe) or a syringe into which the liquid medicine is suctioned when it is used. Also, the syringe 4 can be a dual chamber syringe in which a freeze-dried preparation and a solvent can be filled and mixed in the syringe.

In the aforementioned embodiment, the stopper flange 201 is formed into an annular shape but is not limited to this configuration. The stopper flange 201 can be formed into, for example, a strip shape or a polygonal shape as long as the user can hook the fingers when the user presses the plunger 41.

In the aforementioned embodiment, the rod insertion part 210 can be moved forward and rearward in the moving direction, but is not limited to this configuration. The rod insertion part 210 can be configured to, for example, only move toward the front side (i.e., move forward) in the moving direction. However, the rod insertion part 210 movable in both of forward and rearward directions in the moving direction improves the operability in the setting of the amount of dosage.

Although not specifically mentioned in the aforementioned embodiment, the shape of the receiving part 211 can be a shape extending radially outward of the rod insertion part 210 from the entire circumference of the outer peripheral surface of the rod insertion part 210, that is, can be a shape other than the flange shape. However, the rear end surface of the receiving part 211 serves as a part to indicate a pressing amount or distance (i.e., the setting of the amount of dosage) of the plunger 41 and thus is preferably a flat surface.

In the aforementioned embodiment, the setting restriction part 3 is configured to restrict the change in the setting of the amount of dosage by restricting the rotational motion of the setting operation part 20 and the sliding motion of the movable receiving part 21, but is not limited to this configuration. The setting restriction part 3 can be configured to restrict the change in the setting of the amount of dosage by, for example, releasing the engagement of the setting operation part 20 with the interlock rotating part 230 in the circumferential direction, that is, by preventing the setting operation part 20 from rotating along with rotation of the interlock rotating part 230.

In the aforementioned embodiment, the restriction operation part 30 is configured to switch from the permissible state to the restricted state as it moves in the rearward direction and switch from the restricted state to the permissible state as it moves in the forward direction, but is not limited to this configuration. The restriction operation part 30 can be configured to, for example, switch from the restricted state to the permissible state as it moves in the rearward direction and switch from the permissible state to the restricted state as it moves in the forward direction.

In the aforementioned embodiment, the restriction operation part 30 is configured to slide in the moving direction to thereby switch between the restricted state and the permissible state, but is not limited to this configuration. The restriction operation part 30 can be configured to, for example, rotate in the circumferential direction around the plunger 41 to switch between the restricted state and the permissible state. In such a case, the setting operation part 20 is preferably configured to be slidable in the moving direction so that this slide enables to set the amount of dosage.

REFERENCE SIGNS LIST

1: Dosage adjuster
2: Dosage setting part
3: Setting restriction part
4: Syringe
20: Setting operation part
21: Movable receiving part
22: Connecting part
23: Interlock mechanism
24: Scale
30: Restriction operation part
31: Anti-rotation part
32: Movement restriction part
40: Barrel
41: Plunger
200: Operation cylinder
201: Stopper flange
204: Protrusion
210: Rod insertion part
210*a*: Long hole
211: Receiving part
220: Fixing part
221: Guide part
221*a*: Extending part
221*b*: Protruding part
222: Attachment part
230: Interlock rotating part
230*a*: Fitting groove
231: Power transmission part
231*a*: Inward screw part
231*b*: Outward screw part
301: Interfering projection
310: Front end part
311: Rear end part
312: Anti-rotation projection
320: Flexible piece part
321: Bulging part
400: Cylindrical part
401: Nozzle
402: Flange
410: Rod part
411: Gasket
412: Operation part

The invention claimed is:

1. A dosage adjuster for a syringe comprising:

a dosage setting part configured to set an amount of dosage dischargeable out of a liquid medicine filled in the syringe; and a setting restriction part configured to switch between a restricted state in which change in setting of the amount of dosage set by the dosage setting part is restricted and a permissible state in which the change in the setting of the amount of dosage by the dosage setting part is permissible, wherein the dosage setting part comprises a setting operation part configured to rotate in a circumferential direction around a central axis of a plunger of the syringe to thereby initiate change in the setting of the amount of dosage, the setting restriction part comprises a restriction operation part configured to move in a moving direction in which the plunger moves forward and rearward to thereby switch between the restricted state and the permissible state, and an anti-rotation part having a cylindrical shape and fixed to the cylinder in a state where the rotation in the circumferential direction is restricted, the restriction operation part is integrated with the setting operation part, and is configured to be inserted into the anti-rotation part, interfering projections are formed on an outer surface of the outer surface of the restriction operation part, anti-rotation projections are formed on an inner surface of the anti-rotation part, the restriction operation part is configured to restrict rotation of the setting restriction part by the movement toward one side in the moving direction to cause the interfering projections and the anti-rotation projections to be engaged with each other, and permit the rotation of the setting restriction part by the movement toward another side in the moving direction to cause the interfering projections and the anti-rotation projections to be disengaged from each other.

2. The dosage adjuster for the syringe according to claim 1, wherein the moving direction toward the one side of the restriction operation part coincides with the rearward direction in which the plunger is moved rearward, and the moving direction toward the other side of the restriction operation part coincides with the forward direction in which the plunger is moved forward, and the restriction operation part comprises a stopper flange that extends radially outward and orthogonal to the central axis of the plunger.

3. The dosage adjuster for the syringe according to claim 2, further comprising:

an operation cylinder that has a cylindrical shape and is configured to, in a state where the syringe is inserted through the operation cylinder, be rotatable in the circumferential direction around the plunger and slidable in the moving direction in which the plunger is moved forward and rearward, wherein the operation cylinder comprises the dosage setting part and the setting restriction part.

4. The dosage adjuster for the syringe according to claim 1, wherein the dosage setting part comprises a movable receiving part that is arranged on an opposite side of a front surface of a flange of the plunger of the syringe and is movable forward in the moving direction of the plunger from a position in contact with the front surface of the flange, and the movable receiving part is configured to set the amount of dosage on the basis of a distance away from the flange in the forward direction.

* * * * *